United States Patent
Magen et al.

(10) Patent No.: US 12,070,619 B2
(45) Date of Patent: Aug. 27, 2024

(54) RADIOTHERAPY APPLICATOR WITH PERPENDICULAR OR ANGLED RADIAL DISPENSING

(71) Applicant: ALPHA TAU MEDICAL LTD., Jerusalem (IL)

(72) Inventors: Ofer Magen, Hod Hasharon (IL); Niv Dana, Hod HaSharon (IL); Oded Aldaag, Rehovot (IL); Yoav Roa, Yeruham (IL); Itzhak Kelson, Tel Aviv (IL); Amnon Gat, Matan (IL); Robert Den, Merion Station, PA (US)

(73) Assignee: ALPHA TAU MEDICAL LTD., Jerusalem (IL)

( * ) Notice: Subject to any disclaimer, the term of this patent is extended or adjusted under 35 U.S.C. 154(b) by 147 days.

(21) Appl. No.: 17/852,610

(22) Filed: Jun. 29, 2022

(65) Prior Publication Data
US 2023/0001232 A1    Jan. 5, 2023

Related U.S. Application Data

(60) Provisional application No. 63/216,565, filed on Jun. 30, 2021.

(51) Int. Cl.
*A61N 5/10*    (2006.01)

(52) U.S. Cl.
CPC ......... *A61N 5/1001* (2013.01); *A61N 5/1007* (2013.01); *A61N 2005/1011* (2013.01)

(58) Field of Classification Search
CPC ................ A61N 5/1001; A61N 5/1007; A61N 2005/1011
See application file for complete search history.

(56) References Cited

U.S. PATENT DOCUMENTS

| 4,532,935 A | 8/1985 | Wang |
| 4,766,906 A | 8/1988 | Wang |

(Continued)

FOREIGN PATENT DOCUMENTS

| CN | 2647349 Y | 10/2004 |
| CN | 202036681 U | 11/2011 |

(Continued)

OTHER PUBLICATIONS

International Application # PCT/IB2022/055322 filed Jun. 8, 2022.

(Continued)

*Primary Examiner* — Christine H Matthews
*Assistant Examiner* — Marc D. Honrath
(74) *Attorney, Agent, or Firm* — MEITAR PATENTS LTD.

(57) ABSTRACT

A device for implanting radiotherapy seeds in a tumor. The device includes a delivery tube having a distal end designed to enter the tumor, and defining an internal channel and an elongate applicator carrying one or more radiotherapy seeds each having a length of at least 1 millimeter, the applicator passing through the internal channel of the delivery tube. When a distal end of the elongate applicator is near a distal end of the delivery tube, it assumes an angle relative to an axis of the delivery tube, such that seeds ejected from the elongate applicator enter the tumor at an angle relative to the axis of the delivery tube.

11 Claims, 10 Drawing Sheets

(56) References Cited

U.S. PATENT DOCUMENTS

| | | | |
|---|---|---|---|
| 4,997,424 A | 3/1991 | Little | |
| 6,159,143 A | 12/2000 | Lennox | |
| 6,210,315 B1 | 4/2001 | Andrews et al. | |
| 6,213,932 B1 | 4/2001 | Schmidt | |
| 6,264,600 B1 * | 7/2001 | Grimm | A61N 5/1027 600/7 |
| 6,270,472 B1 | 8/2001 | Antaki et al. | |
| 6,752,753 B1 | 6/2004 | Hoskins et al. | |
| 7,041,047 B2 * | 5/2006 | Gellman | A61N 5/1027 600/3 |
| 8,365,721 B2 | 2/2013 | Larsen et al. | |
| 8,795,145 B2 * | 8/2014 | Hermann | A61N 5/1027 600/3 |
| 8,834,837 B2 | 9/2014 | Kelson et al. | |
| 10,543,379 B2 | 1/2020 | Hingston et al. | |
| 2003/0199726 A1 | 10/2003 | Gatto | |
| 2003/0220533 A1 | 11/2003 | Pedersen et al. | |
| 2005/0038312 A1 | 2/2005 | Green et al. | |
| 2005/0209499 A1 | 9/2005 | Elliott et al. | |
| 2006/0085068 A1 | 4/2006 | Barry | |
| 2007/0055172 A1 | 3/2007 | Ratnakar | |
| 2008/0207982 A1 | 8/2008 | Elliott et al. | |
| 2009/0112161 A1 | 4/2009 | Maerten et al. | |
| 2009/0112261 A1 | 4/2009 | Barry | |
| 2009/0136422 A1 | 5/2009 | Kelson et al. | |
| 2009/0193764 A1 | 8/2009 | Elliott et al. | |
| 2009/0234176 A1 | 9/2009 | Lebovic et al. | |
| 2010/0280494 A1 | 11/2010 | Matsuura et al. | |
| 2010/0292711 A2 * | 11/2010 | Selis | A61B 90/98 606/142 |
| 2011/0257459 A1 | 10/2011 | Sutton et al. | |
| 2013/0204124 A1 | 8/2013 | Duindam et al. | |
| 2014/0121445 A1 | 5/2014 | Fontenot et al. | |
| 2015/0273207 A1 | 10/2015 | Tran et al. | |
| 2015/0273237 A1 | 10/2015 | Raus et al. | |
| 2016/0136454 A1 | 5/2016 | Kader et al. | |
| 2018/0296855 A1 | 10/2018 | Lohrenz et al. | |
| 2018/0345038 A1 | 12/2018 | Kelson et al. | |
| 2020/0086140 A1 | 3/2020 | Stoianovici et al. | |
| 2020/0101049 A1 | 4/2020 | Seward | |
| 2020/0146757 A1 | 5/2020 | Fenech et al. | |
| 2020/0261740 A1 | 8/2020 | Baker et al. | |
| 2020/0345980 A1 | 11/2020 | Serina et al. | |
| 2020/0406059 A1 | 12/2020 | Kelson et al. | |
| 2021/0145445 A9 | 5/2021 | Goldsmith | |
| 2021/0146154 A1 | 5/2021 | Racenet et al. | |
| 2022/0117468 A1 | 4/2022 | Barry et al. | |
| 2022/0142500 A1 | 5/2022 | Greenburg et al. | |

FOREIGN PATENT DOCUMENTS

| | | |
|---|---|---|
| CN | 202961502 U | 6/2013 |
| CN | 203898926 U | 10/2014 |
| CN | 111249612 A | 6/2020 |
| CN | 111632261 A | 9/2020 |
| CN | 215781051 U | 2/2022 |
| EP | 3708081 A1 | 9/2020 |
| JP | H0394773 A | 4/1991 |
| KR | 20140016030 A | 2/2014 |
| RO | 134941 A2 | 5/2021 |
| WO | 03039463 A2 | 5/2003 |
| WO | 2011053908 A1 | 5/2011 |
| WO | 2015136192 A1 | 9/2015 |
| WO | 2020188508 A1 | 9/2020 |
| WO | 2022189987 A1 | 9/2022 |

OTHER PUBLICATIONS

International Application # PCT/IB2022/052084 Search Report dated May 22, 2022.

International Application # PCT/IB2022/056032 Search Report dated Aug. 21, 2022.

U.S. Appl. No. 18/263,716 Office Action dated Feb. 15, 2024.

* cited by examiner

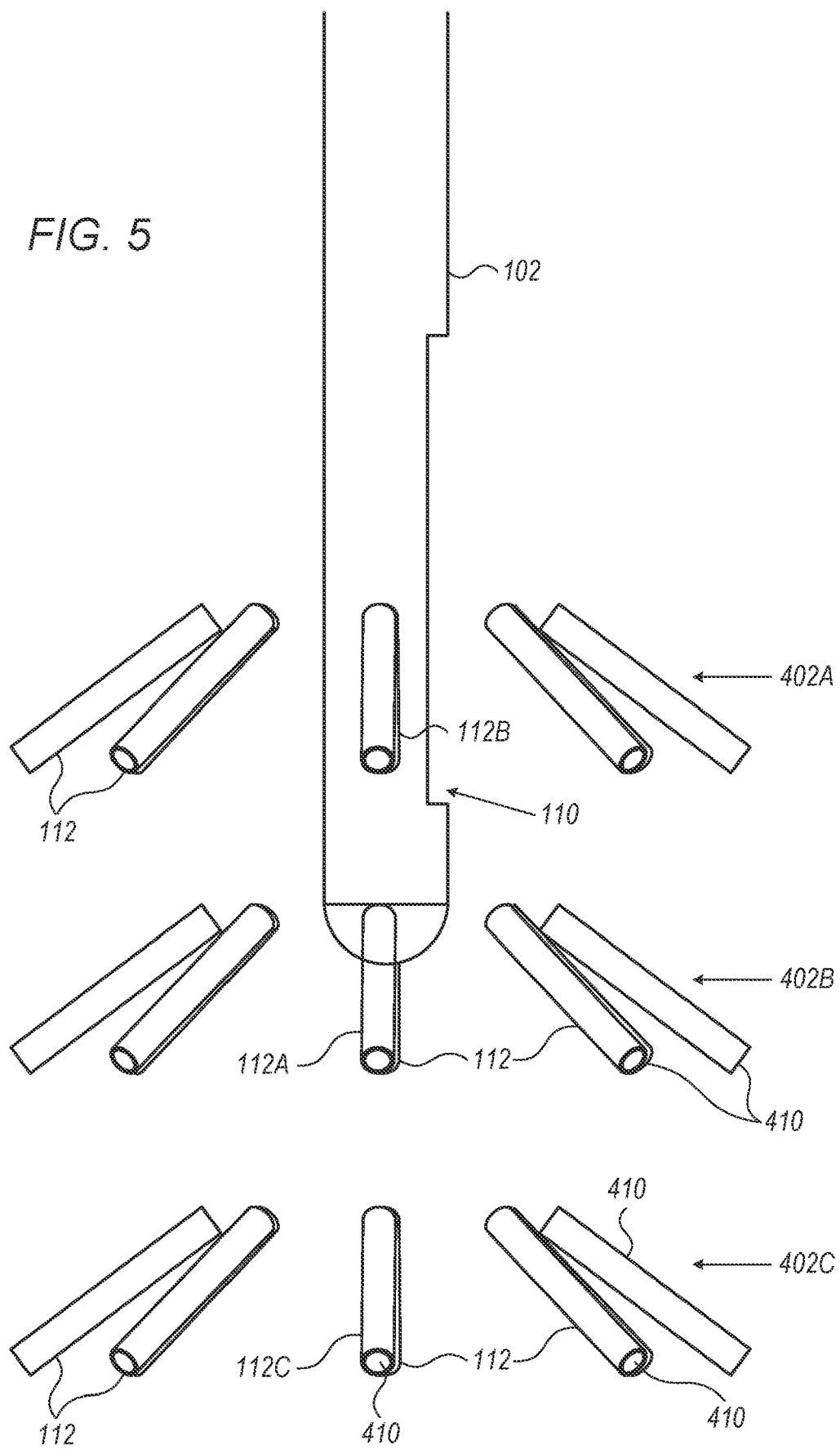

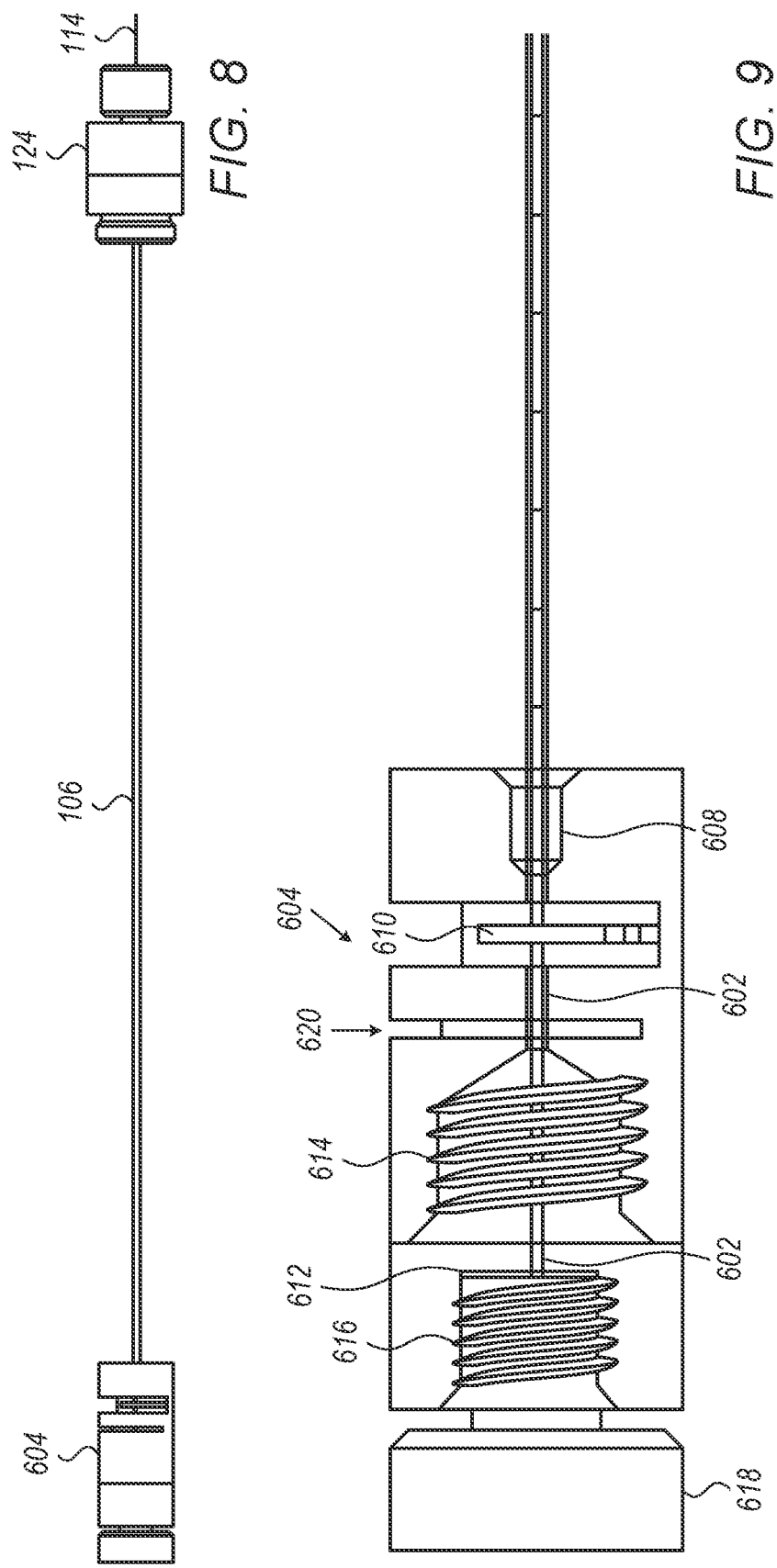
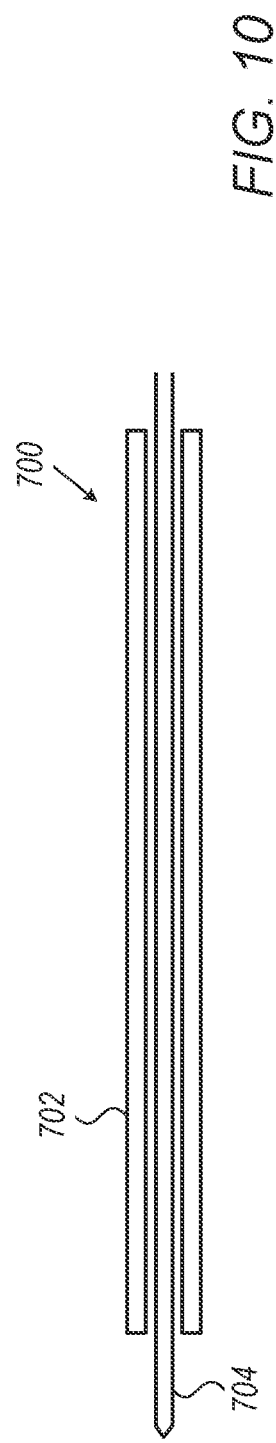
FIG. 8
FIG. 9
FIG. 10

RADIOTHERAPY APPLICATOR WITH PERPENDICULAR OR ANGLED RADIAL DISPENSING

CROSS-REFERENCE TO RELATED APPLICATIONS

The present application claims the benefit of U.S. Provisional Application 63/216,565, filed on Jun. 30, 2021, whose disclosure is incorporated herein by reference in its entirety.

FIELD OF THE INVENTION

The present invention relates generally to radiotherapy and particularly to methods and devices for dispensing of sources of alpha-emitting radioisotopes in tumors.

BACKGROUND OF THE INVENTION

Ionizing radiation is commonly used in the treatment of certain types of tumors, including malignant cancerous tumors, to destroy their cells.

Diffusing alpha-emitters radiation therapy (DaRT), described for example in U.S. Pat. No. 8,834,837 to Kelson, extends the therapeutic range of alpha radiation, by using radium-223 or radium-224 atoms, which generate chains of several radioactive decays.

In order for the treatment of a tumor to be effective, DaRT seeds employed in the treatment should be implanted throughout the tumor at small distances, e.g., less than 5 millimeters, from each other. Some tumors are easily accessible externally by a physician for implantation of the seeds, while other tumors are in internal organs.

US patent publication 2022/00500 to Greenburg et al., describes an integrated multi-functional endoscopic tool including a needle, which can be used to implant seeds for brachytherapy.

Glioblastoma ("GBM") is a cancerous tumor located in the brain, which, due to its proximity to core nerve and brain cells and its neural connection to the spinal cord, has been a particularly intractable form of cancer to effectively treat without harming or killing the patient. As a consequence, GBM is one of the deadliest forms of cancer with few availing treatment options and a GBM prognosis bears dim survival prospects.

US patent publication 2013/0204124 to Duindam et al. describes a flexible needle which can be used to deliver radioactive seeds at internal locations that would be problematic to access via a straight path.

SUMMARY OF THE INVENTION

Embodiments of the present invention relate to implanting a plurality of radiotherapy seeds into a tumor, through a single insertion hole for introducing a seed applicator into the tumor.

There is therefore provided in accordance with an embodiment of the present invention, a device for implanting radiotherapy seeds in a tumor, comprising a delivery tube having a distal end designed to enter the tumor, and defining an internal channel and an elongate applicator carrying one or more radiotherapy seeds each having a length of at least 1 millimeter, the applicator passing through the internal channel of the delivery tube, wherein when a distal end of the elongate applicator is near a distal end of the delivery tube, it assumes an angle relative to an axis of the delivery tube, such that seeds ejected from the elongate applicator enter the tumor at an angle relative to the axis of the delivery tube.

Optionally, the device includes a stylet within the elongate applicator designed to push the one or more radiotherapy seeds relative to the elongate applicator so as to eject the seeds from the elongate tube into the tumor, when the distal end of the elongate applicator is in the tumor. Optionally, the device includes a stylet handle configured to accurately push the stylet relative to the elongate applicator by an extent equal to the length of a seed at the distal end of the elongate applicator. Optionally, the stylet handle is configured to push the stylet while holding the elongate applicator stationary. Alternatively, the stylet handle is configured to hold the stylet stationary while retracting the elongate applicator.

Optionally, the distal end is configured to eject the seeds from the elongate applicator at an angle of at least 5° relative to the axis of the delivery tube. Optionally, wherein the distal end is configured to eject the seeds from the elongate applicator at an angle of at least 30° relative to the axis of the delivery tube. Optionally, the distal end is configured to eject the seeds from the elongate applicator at an angle of at least 45° relative to the axis of the delivery tube. Optionally, the distal end is configured to eject the seeds from the elongate applicator at an angle of less than 25° relative to the axis of the delivery tube. Optionally, the distal end is configured to eject the seeds from the elongate applicator at an angle of less than 15° relative to the axis of the elongate tube.

In some embodiments, the elongate applicator comprises a nitinol tube. Optionally, the delivery tube is configured to be rotated within the tumor. Optionally, the device includes a rotation mechanism configured to rotate the delivery tube within the tumor by a prescribed angle. Optionally, the internal hollow channel is configured to carry and eject seeds, having a length of at least 5 millimeters. Optionally, the distal end of the elongate tube is configured to assume a bended shape with an angle relative to the axis of the elongate tube, when free of external forces. Optionally, the delivery tube comprises a side window toward its distal end, and wherein the applicator is configured to eject the one or more radiotherapy seeds through the side window. Optionally, the delivery tube comprises two concentric tubes which are rotated relative to each other to open and close for window. Optionally, the delivery tube comprises a slope near the window, which causes the distal end of the elongate applicator tube to assume the angle relative to the axis of the elongate tube. Optionally, the elongate applicator carries at least three seeds or even at least five seeds.

There is further provided in accordance with an embodiment of the present invention, a method of inserting seeds into a tumor, comprising inserting a delivery tube to a first depth in the tumor, ejecting a plurality of seeds from the delivery tube into the tumor, while the delivery tube is at the first depth, wherein each of the plurality of seeds is ejected at an angle relative to an axis of the delivery tube, and wherein the plurality of seeds are ejected in at least two different radial angles and moving the delivery tube to a second depth in the tumor and ejecting one or more seeds from the delivery tube into the tumor at the second depth.

Optionally, ejecting the plurality of seeds comprises ejecting the seeds at an angle of at least 10° relative to the axis of the delivery tube. Optionally, ejecting the plurality of seeds comprises rotating the delivery while the delivery tube is at the first depth, in order to eject seeds to different radial angles. Optionally, ejecting one or more seeds from the delivery tube into the tumor at the second depth comprises ejecting in the second depth shorter seeds than in the first depth. Optionally, a same number of seeds are ejected from the first and second depths. Optionally, the seeds in the first depth are ejected at different radial angles than the seeds of the second depth.

There is further provided in accordance with an embodiment of the present invention, a method of planning a radiotherapy treatment of a tumor, comprising acquiring an image of the tumor, determining a type of the tumor, determining a coverage of the entire tumor by one or more cylindrical regions, having a diameter not greater than a predetermined maximal diameter corresponding to the determined tumor type, for each of the one or more cylindrical regions, selecting a number of layers of seeds and a number of seeds in each of the layers, required to provide a sufficient radiation dose to every point in the cylindrical region, wherein each layer includes a plurality of seeds to be implanted from a delivery tube when a distal end of the delivery tube is located at a single point; and presenting a plan for implanting seeds in the tumor, responsive to the determined cylindrical regions, the number of layers of seeds and the number of seeds in each of the layers. Optionally, the layers are cone-shaped layers. Optionally, the predetermined maximal diameter is at least 10 millimeters.

BRIEF DESCRIPTION OF THE DRAWINGS

FIG. 5 is a schematic illustration of a layout of seeds, in accordance with an embodiment of the present invention;

FIG. 8 is a schematic illustration of a preloaded applicator during delivery, before use, in accordance with an embodiment of the present invention;

FIG. 9 is a schematic illustration of a distal hub of an applicator during delivery, in accordance with an embodiment of the invention; and FIG. 10 is a cross section of a delivery tube system, in accordance with anther embodiment of the invention.

DETAILED DESCRIPTION OF EMBODIMENTS

Figure 1:
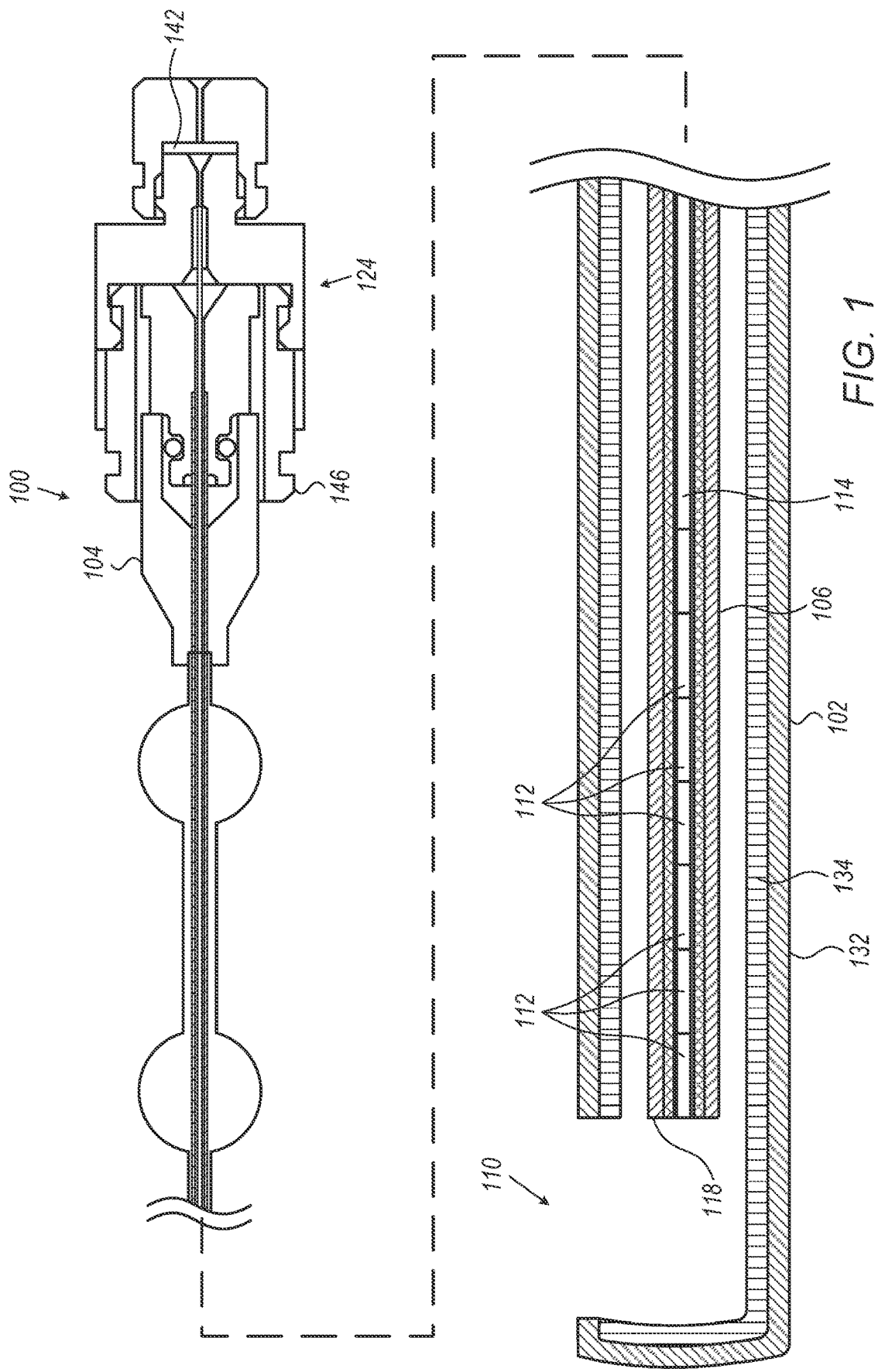
FIG. 1 is a schematic cross-section of a medical probe, for use in implanting radiotherapy seeds in a patient, in accordance with an embodiment of the invention.

An aspect of some embodiments of the invention relates to a method of implanting radiotherapy seeds into a tumor, in which a distal end of an applicator is inserted to one or more pivot points in the patient, and from each of the one or more pivot points a plurality of seeds are dispensed at different angles. In some embodiments, the plurality of elongate seeds dispensed at different angles from a single pivot point include seeds dispensed in at least three different radial angles, at least four different radial angles or even at least six different radial angles, forming a cone, flower or sun shape. The seeds are distributed evenly or unevenly around the single pivot point, for example depending on the shape of the tumor.

Implanting elongate seeds at different angles from a single pivot point results in having a different distance between the seeds at their proximal end near the single point and at their distal ends farther from the single point. This difference in distance between different portions of the seeds is not desired, because the destruction range of the radiation from the seeds decreases sharply with the range from the seed. Applicant, however, has determined that the sun shaped arrangement can provide sufficient radiation to destroy a tumor, and the advantage in simplifying the implanting of the seeds by reducing the number of insertion points of the delivery tube into the patient, outweighs the irregularity of the radiation distribution. Minimizing the number of insertion points is particularly important for glioblastoma tumors in the brain, which is delicate tissue in which it is important to minimize bleeding. Nonetheless, embodiments of the invention could be advantageous in treating other tumors requiring percutaneous implantation of seeds, such as lung, pancreas and liver tumors.

An aspect of some embodiments of the present invention relates to a probe for implanting radioactive seeds into a tumor. The probe comprises an outer delivery tube whose distal end is led into the tumor, and an elongate applicator carrying one or more radiotherapy seeds, which passes through an inner channel of the outer delivery tube. The probe is designed such that the distal end of the elongate applicator dispenses seeds at an angle (i.e., an angle different from zero, for example at least 2° or even at least 5°) relative to an axis of the outer delivery tube. Additionally, the probe is designed to allow changing the radial angle at which the elongate applicator dispenses seeds, without taking the outer delivery tube out of the tumor. In some embodiments, the outer delivery tube is rotated within the patient, in order to change the radial angle of seed-ejection. Optionally, the elongate applicator rotates with the outer delivery tube. Alternatively, the elongate applicator does not rotate with outer delivery tube, but rather assumes an angle relative to the outer delivery tube, due to an internal slope or bulge in the delivery tube, such that rotation of the applicator is unnecessary. Further alternatively, the outer delivery tube remains stationary and the elongate applicator is rotated. In some embodiments, the applicator has a wide angle of rotation of at least 180°, at least 270°, at least 300° or even up to a full 360°. The applicator optionally allows an operator to dispense multiple seeds radially from a single insertion depth of the applicator, where each of the seeds is dispensed at a different radial angle. The operator optionally can adjust the angle between the seeds, such that the seeds are distributed evenly or unevenly around the applicator. The operator can potentially dispense seeds at multiple depths along the axis of insertion as the applicator is inserted or removed, rather than inserting an applicator repeatedly to dispense the seed directly beneath the applicator. Aspects of the invention thus allow for minimally invasive application of radiotherapy seeds in GBM or other tumors and provides an alternative delivery mechanism to existing apparatus.

FIG. 1 is a schematic cross-section of a medical probe 100, for use in implanting radiotherapy seeds in a patient, in accordance with an embodiment of the invention. Probe 100 comprises an external delivery tube 102 and an internal applicator 106, which passes through an inner channel of delivery tube 102.

Internal applicator 106 defines an internal channel which carries at its distal end a plurality of seeds 112, which are to be delivered into a tumor. Proximally to the seeds 112, the internal channel of applicator 106 carries a stylet 114, which is used to push the seeds 112 into the tumor.

External delivery tube 102 has at its distal end a side window 110, through which a distal end 118 of applicator 106 exits external delivery tube 102 and/or ejects seeds 112 into the tumor. In some embodiments, delivery tube 102 is formed of two concentric tubes, external tube 132 and internal tube 134 which each has an opening for window 110. When tubes 132 and 134 are aligned, window 110 is open, while when tubes 132 and 134 are misaligned, window 110 is closed. At its proximal end, external tube 132 comprises a hub 104. Likewise, internal tube 134 has a hub 128 at its proximal end. Window 110 is opened and closed by rotating hub 128 relative to hub 104. In some embodiments, an O-ring 144 tightens the coupling between hub 104 and hub 128.

In some embodiments, applicator 106 has a hub 124 at its proximal end, and hub 124 is configured to couple to hub 128. Optionally, hub 124 is designed with an internal chamber which fits over hub 128, in a first state, in which the distal end of internal applicator 106 exits window 110. In a second state, hub 124 is retracted such that its distal lip 146 couples to a proximal area of hub 128. Optionally, in the second state, rotation of hub 124 rotates hub 128 along with internal tube 134. Thus, a physician can open and close window 110 by rotating hub 124. In some embodiments, a suitable notch (not shown) prevents moving hub 124 into the first state unless window 110 is open.

Hub 124 is shown with a silicone sheet 142, which seals the proximal end of applicator 106 during delivery, before use, as discussed hereinbelow.

In some embodiments, external delivery tube 102 comprises a biopsy needle. In other embodiments, external delivery tube 102 comprises a camera carrying probe, such as an endoscope or bronchoscope. In still other embodiments, external delivery tube 102 comprises any other suitable medical probe. External delivery tube 102 comprises a material which is clinically safe for insertion into a body organ for which it is intended. For example, when medical probe 100 is configured for treatment of glioblastoma, external delivery tube 102 is designed for safe insertion into brain tissue. Probe 100 may be used for other cancers, such as hepatic cell carcinoma. In some embodiments, external delivery tube 102 comprises a straight rigid tube. Alternatively, external delivery tube 102 is flexible, in order to pass through blood vessels or other winding paths in the patient. In accordance with this alterative, the axis of external delivery tube 102 is taken as the axis of a segment closes to a distal tip of external delivery tube 102.

Elongate applicator 106 comprises a biocompatible tube formed of a material which is optionally flexible or otherwise pre-configured into a specific shape to achieve flexibility. In some embodiments, elongate applicator 106 comprises a polyimide, such as Kapton.

Elongate applicator 106 and external delivery tube 102 optionally have a length of at least 250 millimeters, such as 300 millimeters. Elongate applicator 106 optionally has an outer diameter of about 1.25 mm and an inner diameter of about 0.85 mm Delivery tube 102 optionally has a diameter of between 1.5-2.5 millimeters, for example between 1.8-2.2 millimeters, e.g., about 2.1 millimeters. It is noted that other sizes may be used, depending on the task to be carried out.

In some embodiments, stylet 114 has different levels of rigidity along its length. In a proximal portion of the stylet 114, the stylet has a high rigidity sufficient to push the seeds 112 without collapsing. A distal portion of stylet 114 is less rigid, so that it can conform to the bend in applicator 106.

Figure 2:
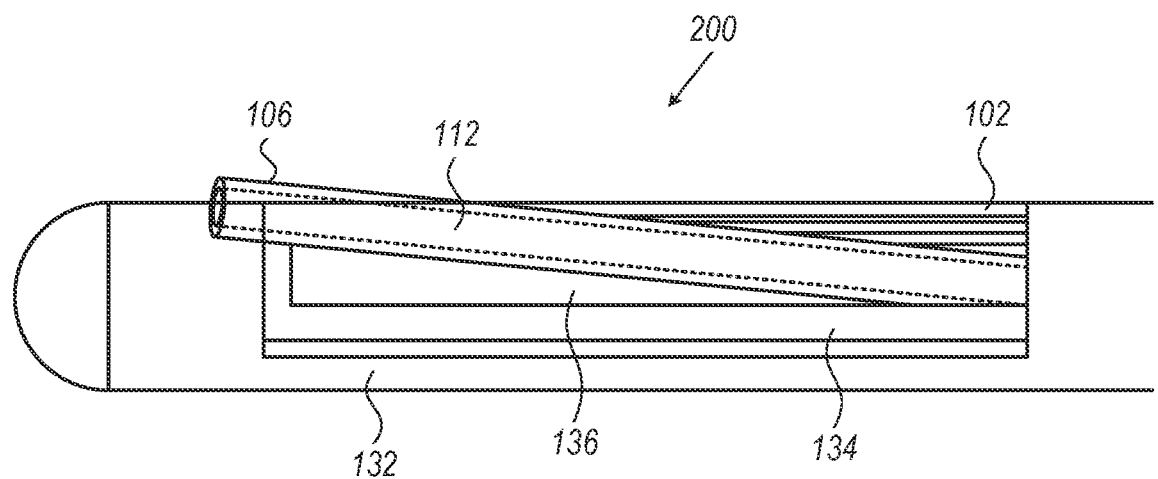
FIG. 2 is a schematic illustration of a distal end of the probe of FIG. 1, in accordance with an embodiment of the invention.

FIG. 2 is a schematic illustration of a distal end 200 of probe 100, in accordance with an embodiment of the invention. Optionally, in order to cause applicator 106 to exit window 110, delivery tube 102 comprises a slanted slope 136 which pushes applicator 106 radially at a desired angle, when applicator 106 is pushed distally. Alternatively to slanted slope 136, applicator 106 is configured with shape memory to have a slant of a desired angle, when not confined by delivery tube 102. In accordance with this alternative, when window 110 is opened, by rotating tubes 132 and 134 to alignment, a distal end of applicator 106 assumes the predetermined angle and exits window 110. In some embodiments, elongate applicator 106 comprises nitinol or any other material which has shape-memory properties. In other embodiments, flexible navigational wires are used to bend a distal portion of delivery tube 102 near window 110.

As shown, the distal end 118 of applicator 106 forms a relatively small angle relative to an axis of delivery tube 102, for example less than 25°, less than 20°, less than 15°, less than 10°, or even less than 5°. This relatively small angle has the advantage of requiring a relatively small bend in applicator 106 to achieve the angle, such that seeds 112 can easily slide within applicator 106 while the applicator is bent.

In other embodiments, the distal end 118 of applicator 106 forms a larger angle relative to delivery tube 102, for example at least 30°, at least 40°, at least 50° or even at least 60°. In some embodiments, distal end 118 forms an angle of about 90° (e.g., between 85° and 95°) with the axis of applicator 106. Use of such larger angles achieves coverage of a larger area surrounding delivery tube 102 and thus reduces the number of different entrance points of delivery tube 102 into the tumor, to ensure the radiation from the seeds 112 covers the entire tumor. In some embodiments, in order to simplify the passage of the seeds 112 through applicator 106, particularly when the angle between applicator 106 and delivery tube 102 is large, the seeds 112 are flexible, for example made of a flexible material or made thin.

Figure 3:
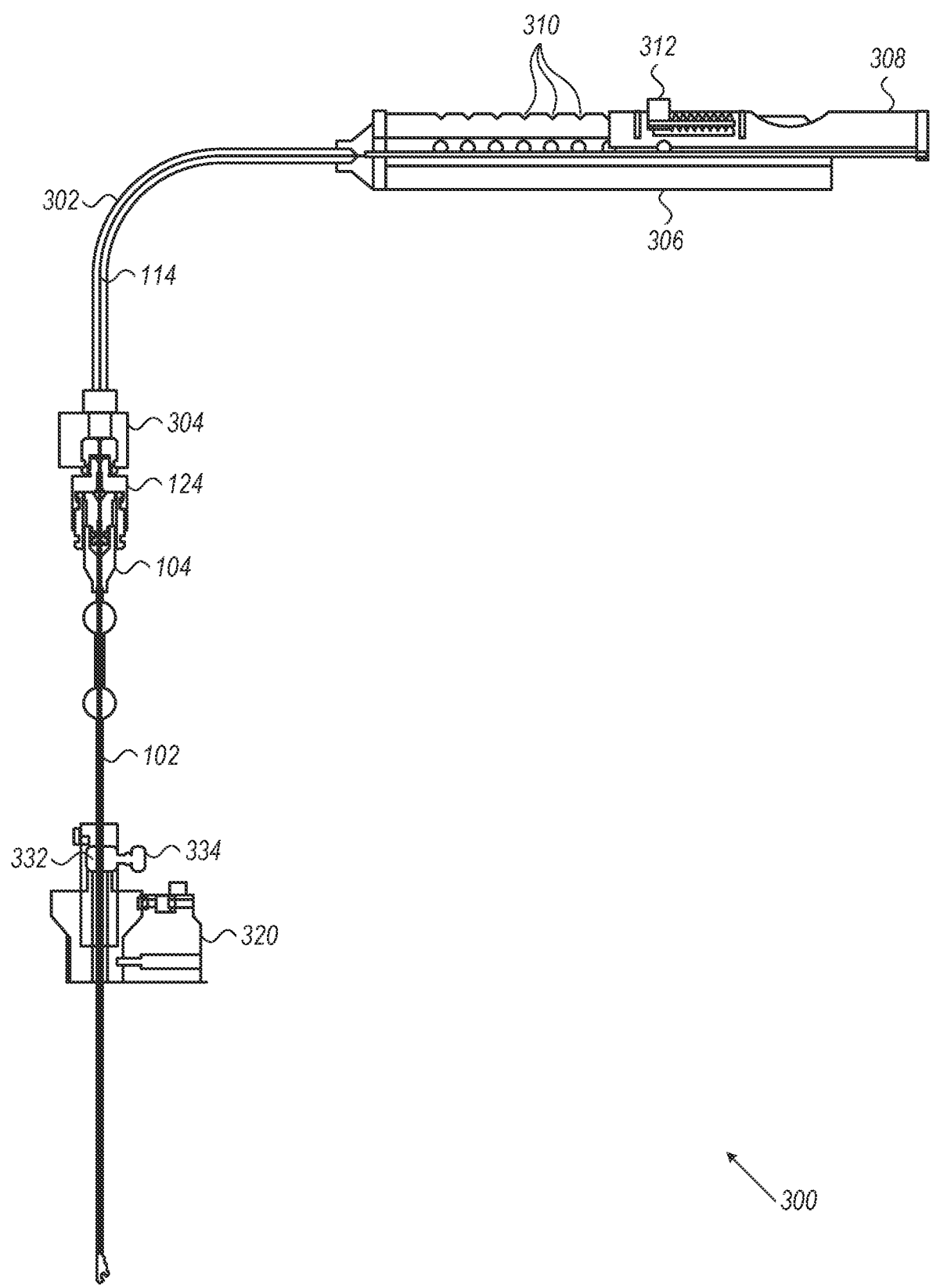
FIG. 3 is a schematic illustration of a system for insertion of seeds into a tumor, in accordance with an embodiment of the invention.

FIG. 3 is a schematic illustration of a system 300 for insertion of seeds into a tumor, in accordance with an embodiment of the invention. System 300 comprises medical probe 100, which as shown in FIG. 1 includes delivery tube 102 and applicator 106 therein. In addition, system 300 optionally includes a stylet guiding tube 302, in which a proximal portion of stylet 114, passes outside of applicator 106. A distal end of stylet guiding tube 302 includes an interface 304 which connects to hub 124 of applicator 106. At its proximal end, stylet guiding tube 302 is connected to a stylet handle 306, which includes a pushing mechanism 308 which is connected to stylet 114, for controllably pushing stylet 114 by a desired amount. Optionally, handle 306 defines notches 310 which are separated from each other by the length of a single seed 112. Pushing mechanism 308 optionally includes a lever (not shown) which fits into notches 310. In order to eject a seed 112, a handle 312 on pushing mechanism 308 is used to pull the lever out of the notch 310 in which it is located, and then pushing mechanism 308 is pushed forward until the lever falls into the following notch 310. In other embodiments, any other suitable mechanism is used to control the movement of pushing mechanism 308 by the length of a single seed or to otherwise control the ejection of seeds 112. In some embodiments, all the seeds 112 used together in a single applicator 106 have the same length and accordingly notches 310 are separated by equal distances matching the lengths of the seeds. Alternatively, an applicator 106 may include seeds of different lengths and the notches are spaced correspondingly with different spacings matching the lengths of the seeds to be released.

In some embodiments, instead of pushing mechanism 308 pushing stylet 114, handle 306 includes a mechanism for retracting applicator 106 by accurate lengths, e.g., the length of a single seed, while holding stylet 114 fixed.

System 300 optionally further includes a clamp 332 which fits on delivery tube 102 and is fastened thereto by a screw 334. A rotation mechanism 320 fits onto clamp 332 and is used to rotate delivery tube 102, with applicator 106, within the tumor.

Figure 4A:
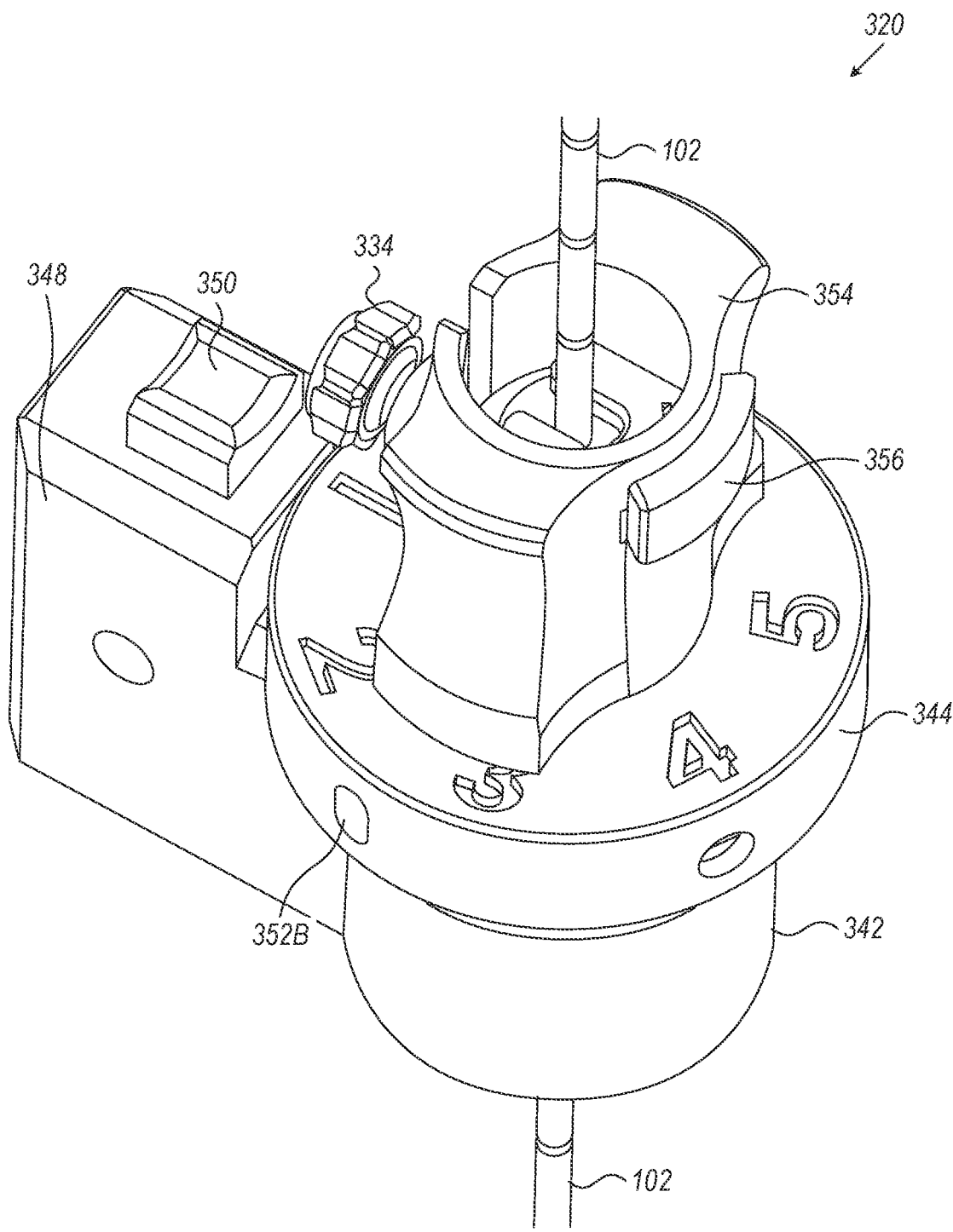
FIGS. 4A-4C are a three-dimensional, exploded and cross-sectional views, respectively, of rotation mechanism, in accordance with an embodiment of the present invention.
Figure 4B:
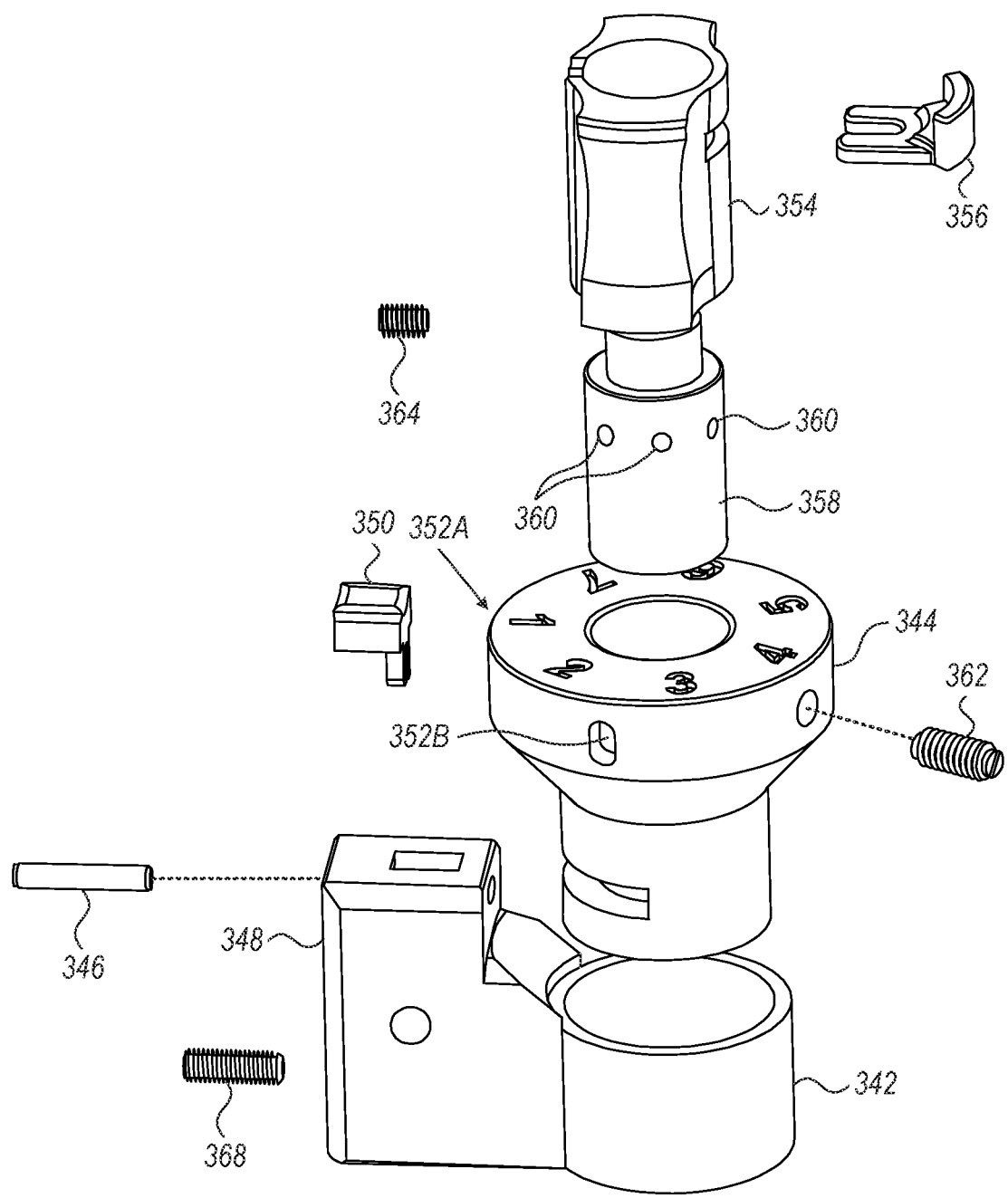
Figure 4C:
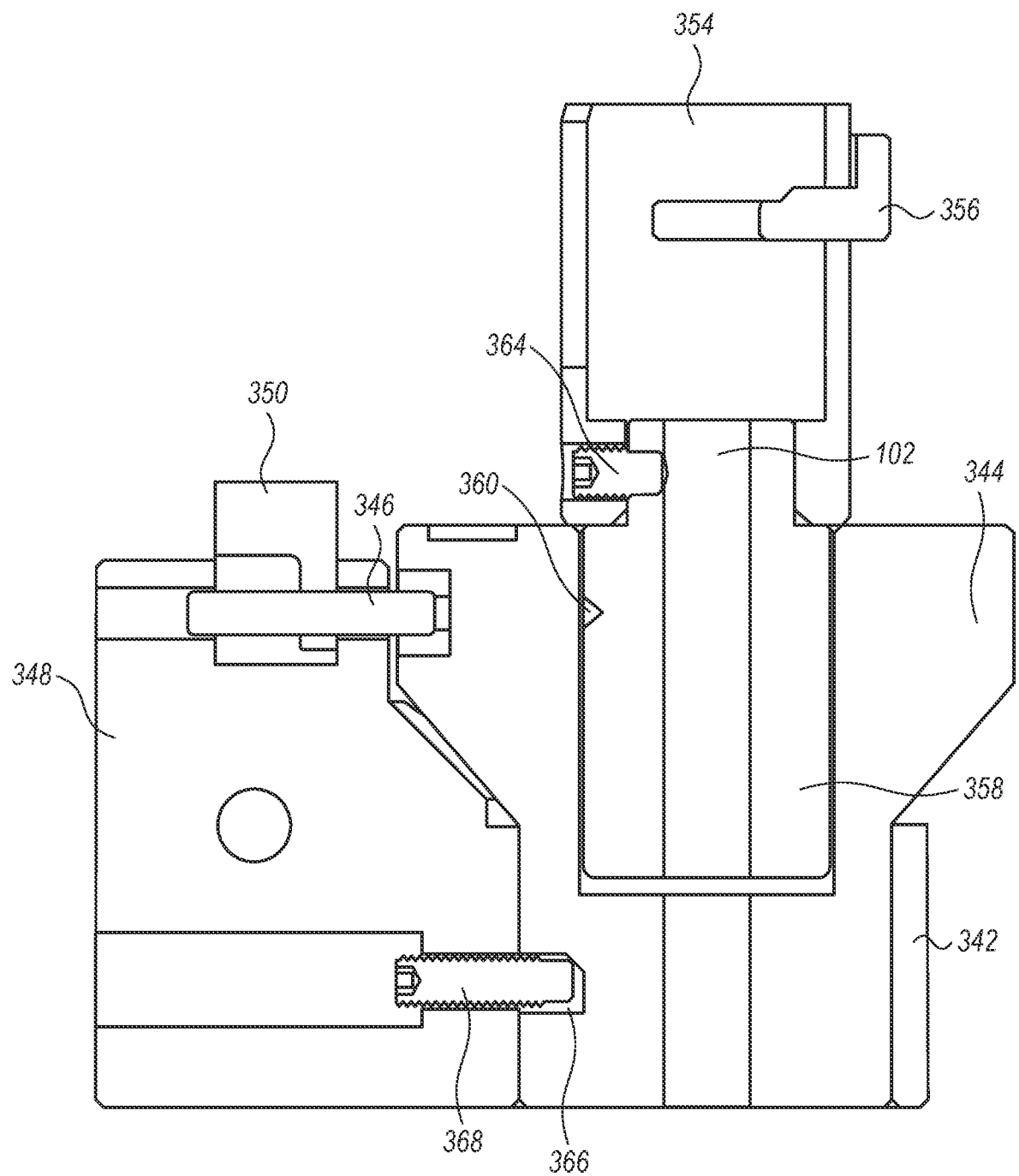

FIGS. 4A-4C are three-dimensional, exploded and cross-sectional views, respectively, of rotation mechanism 320, in accordance with an embodiment of the present invention. Rotation mechanism 320 comprises a stationary base 342 which is designed to be attached to the patient directly or indirectly. For example, when system 300 is used to treat a head tumor, stationary base 342 may be connected to a head frame. An adjustable base 344 is placed within stationary base 342 and is fixed relative to stationary base 342 by a dowel pin 346 located in an internal channel on a side portion 348, of stationary base 342. A shift handle 350 is used to slide dowel pin 346 and push it into one of two or more notches 352 (marked in FIG. 4B as 352A and 352B) designed to receive dowel pin 346 in a manner which locks adjustable base 344 to stationary base 342. In some embodiments, adjustable base 344 defines a slot 366, which runs along a radial area which connects the notches 352. A screw 368 within stationary base 342 optionally locks into slot 366, limiting the relative rotation of bases 342 and 344 to the area between the two or more notches 352.

Rotation mechanism 320 further includes a rotation handle 354 which defines an internal shaft designed to fit on clamp 332. Rotation handle 354 optionally grasps clamp 332 between an upper stopper 356 and an indexing rod 358. Indexing rod 358 is optionally designed to sit within adjustable base 344 and rotate with handle 354. As shown in FIG. 4C, indexing rod 358 is optionally fixed to rotation handle 354 by a screw 364. In some embodiments, indexing rod 358 has apertures 360 at radial angles at which seeds 112 are to be implanted. Optionally, a corresponding ball plunger 362, located in adjustable base 344, fits into apertures 360 and stops rotation of handle 354 at the desired radial angles. Alternatively to ball plunger 362, any other suitable mechanism may be used to stop the rotation of handle 354 at desired radial angles.

Optionally, adjustable base 344 has markings, e.g., digits, which direct the user in rotating handle 354.

In some embodiments, elongate applicator 106 rotates with outer delivery tube 102, for example due to the coupling of their hubs. Alternatively, elongate applicator 106 does not rotate with outer delivery tube, but rather assumes an angle relative to the outer delivery tube, due to an internal slope 136 or bulge in the delivery tube, such that rotation of applicator 106 is unnecessary. Further alternatively, instead of rotating outer delivery tube 102, rotation mechanism 320 is fit onto elongate applicator 106.

It is noted that rotation mechanism 320 provided here is only an example, and any other suitable mechanism for rotating delivery tube 102 and/or elongate applicator 106 may be used. For example, instead of manual rotation of handle 354, a step motor is used to perform the desired amount of rotation. In some embodiments, the step motor is calculated by a processor which accurately controls the rotation based on instructions from an operator. Optionally, the operator indicates the number of seeds to be implanted in each layer, and the processor calculates and implements the rotation angles accordingly.

FIG. 5 is a schematic illustration of a layout 400 of seeds 112, in accordance with an embodiment of the present invention. As shown, seeds 112 are implanted in a tumor from delivery tube 102, in a plurality of cone-shaped layers 402 (marked 402A, 402B and 402C in FIG. 5). The seeds in each layer form a cone-shaped or a sun-shaped configuration. The seeds 112 of each layer 402 are optionally ejected from delivery tube 102 at a same depth in the tumor, at different rotation angles of window 110. Each layer 402 optionally includes seeds 112, in at least four radial angles, at least six radial angles, at least 8 radial angles, at least 10 radial angles or even at least 12 radial angles. Accordingly, the angle between each two radial angles from which seeds 112 were ejected is less than 60°, less than 45°, less than 36° or even less than 30°. The distance between the distal ends 410 of seeds 112 of a single layer 402 is optionally selected such that every point in the tumor is within a sufficiently short distance from the radionuclides on one of the seeds 112. The radial angles in which the seeds 112 are ejected are optionally spaced evenly by about the same angle. Alternatively, for example in irregular tumors, the seeds are spaced unevenly. The seeds 112 in each layer optionally span over 360° around the delivery tube 102. Alternatively, delivery tube 102 is inserted on an edge or close to an edge of a tumor, and seeds 112 are ejected into the tumor over a span of angles suitable for inserting seeds 112 into the tumor.

In some embodiments, the seeds 112 in different layers 402 are ejected at same radial angles, e.g., seeds 112A, 112B and 112C are ejected at same radial angles. Alternatively, the seeds 112 of adjacent layers 402 are ejected at different radial angles to provide a better coverage of the tumor. In one embodiment in accordance with this alternative, the seeds of layer 402B are placed at radial angles half way between the radial angles of the seeds of layers 402A and 402C. This is optionally achieved by moving dowel pin 346 between notches 352A and 352B.

The distance between layers 402 is optionally smaller than 8 millimeters, smaller than 5 millimeters or even smaller than 4 millimeters. In some embodiments, the distance between adjacent layers 402 is such that the distance between the projection of the distal ends of seeds 112 of one layer (e.g., 402B) onto the axis defined by delivery tube 102 and the projection of the proximal ends of seeds 112 of an adjacent layer (e.g., 402C) onto the axis is smaller than a predetermined length. The predetermined length is optionally smaller than 4 millimeters, smaller than 3 millimeters, smaller than 2 millimeters, smaller than 1 millimeter, or even is negative, such that the layers 402 overlap.

In some embodiments, all of seeds 112 have the same length and are ejected at the same angle. Alternatively, seeds of different layers have different lengths and/or are ejected at different angles. For example, two different layers 402 may be generated from a same depth of delivery tube 102 in the tumor, at different ejection angles and possibly with different seed lengths.

Optionally, the layout of seeds 112 is selected such that the distance between any point in a cylinder-shaped region centered around the axis of delivery tube 102, is not distanced from one of the seeds 112 by more than a predetermined maximal distance. The maximal distance is optionally not greater than 2 millimeters, not greater than 1.8 millimeters, or even not greater than 1.6 millimeters.

In one embodiment, each layer includes seven seeds, the seeds have a length of 10 millimeters and the angle of insertion is 15°. The cone shape of each layer optionally has on its narrower side (the upper points of seeds 112 in FIG. 5), a diameter smaller than 4 millimeters, smaller than 3.6 millimeters or smaller than 3.2 millimeters, for example about 3 millimeters. The proximal ends of the seeds are optionally distanced from the outer circumference of delivery tube 102 by at least 0.3 millimeters or even at least 0.5 millimeters, to prevent the seeds 112 from preventing movement of delivery tube 102. The proximal ends of the seeds are optionally distanced from the outer circumference of delivery tube 102 by less than 1 millimeter or even less than 0.8 millimeters, in order to prevent gaps with small radiation doses near the axis of the entrance of delivery tube 102. On its wider side, the cone optionally has a diameter larger than 5 millimeters, or larger than 6 millimeters, for example about 7 millimeters. In this embodiment, for a single insertion of delivery tube 102 into the patient, a cylinder of a radius of 5.5 is covered such that every point in the cylinder has a maximal distance to a nearest seed of 2 millimeters.

Figure 6:
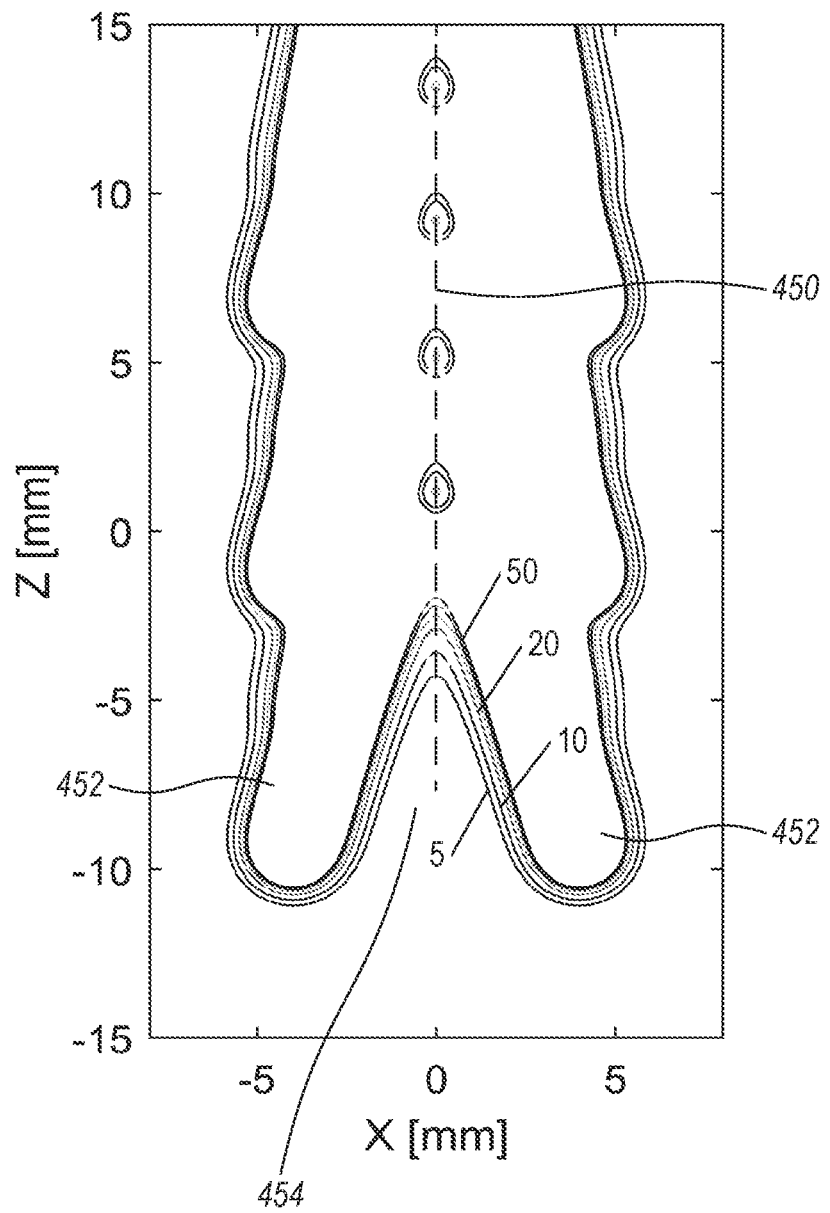
FIG. 6 is a map of an estimated alpha-particle radiation dose reaching a cross section of a Glioblastoma (GBM) tumor in which seeds were implanted in a layout similar to the layout of FIG. 5, in accordance with an embodiment of the present invention

FIG. 6 is a map of an estimated alpha-particle radiation dose reaching a cross section of a Glioblastoma (GBM) tumor in which seeds were implanted in a layout similar to layout 400 of FIG. 5, in accordance with an embodiment of the present invention. The map was created assuming seeds of 6 microcurie per centimeter length and a desorption probability of 45%, which is equivalent to a radon release rate of 2.7 microcurie per centimeter length. The layout is assumed to include six cone-shaped layers 402, each including eight 10-millimeter seeds, and the cone-shaped layers 402 are separated by 4 millimeters.

As can be seen in the map, the layout achieves a dose of more than about 20 Grey in a region of a diameter of about 11 millimeters, centered around the axis 450 of delivery tube 102 used to implant the seeds of the layout. In a lower portion of the region, the region includes a circumferential area 452 surrounding a low dose area 454. In order to avoid this structure, the lowest layer optionally includes shorter seeds, e.g., shorter than 6 millimeters, or shorter than 4 millimeters. Alternatively or additionally, one or more additional seeds 112 are implanted on the axis 450, in area 454.

Figure 7:
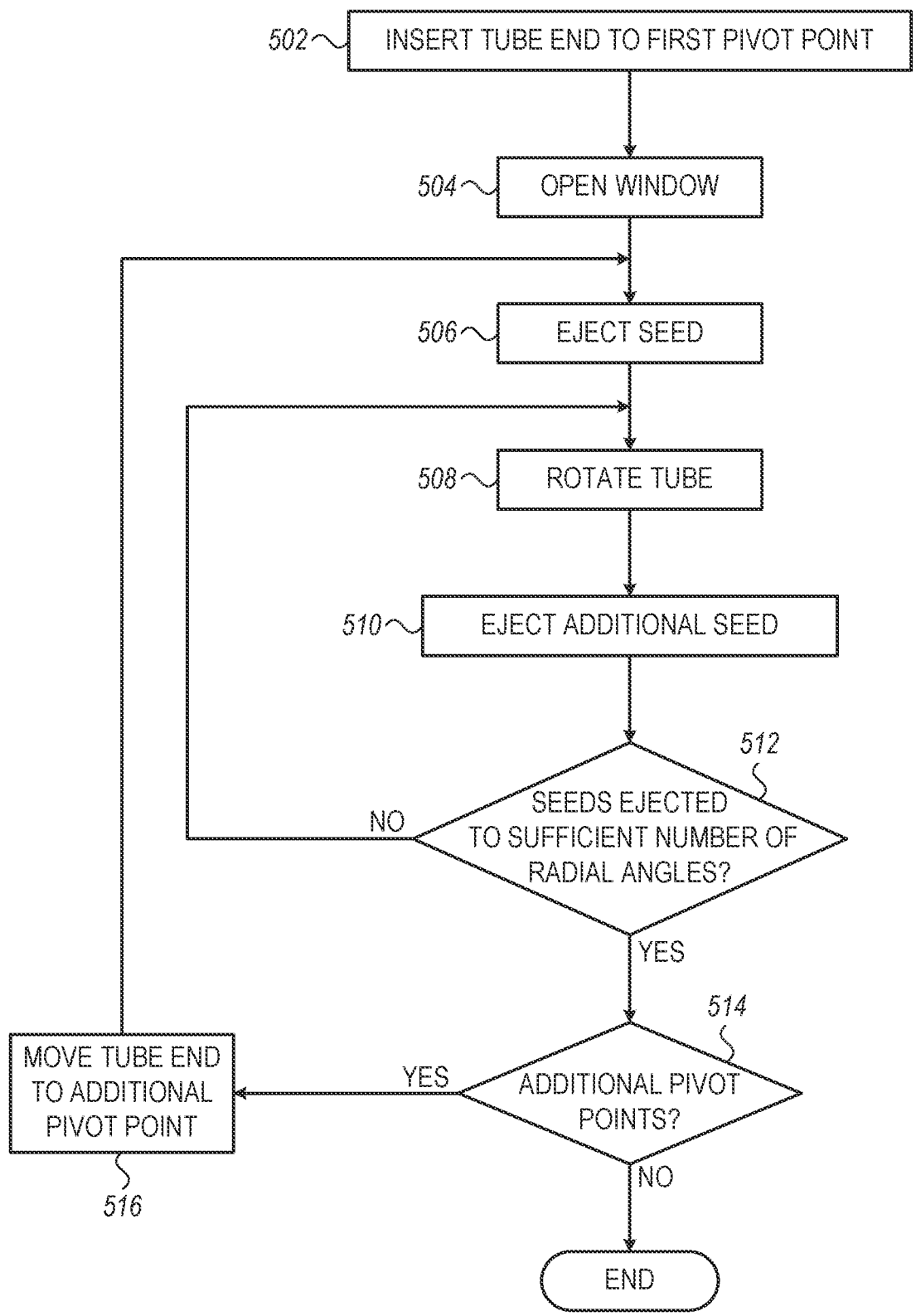
FIG. 7 is a method of placing seeds in a tumor, in accordance with an embodiment of the present invention.

FIG. 7 is a method of placing seeds 112 in a tumor, in accordance with an embodiment of the present invention. The method begins with inserting (502) a distal end of delivery tube 102 into a first point, referred to herein as a first pivot point, in the tumor. Window 110 is then opened (504), and a seed 112 is ejected (506) into the tumor through window 110. The distal end of applicator 106 is then retracted back into delivery tube 102, and the delivery tube 102 with applicator 106 are rotated (508) to a different radial angle, without changing the depth of the delivery tube 102 in the tumor. Another seed is optionally ejected (510) from the first pivot point, at the different radial angle. The rotation (508) and ejection (510) of seeds 112 is optionally repeated until (512) a sufficient number of seeds 112 are ejected from the first pivot point. Then, delivery tube 102 is moved (516) to an additional pivot point and the rotation (508) and ejection (506, 510) of seeds 112 are repeated. Depending (514) on the size of the tumor, delivery tube 102 is further moved (516) to additional pivot points and additional layers 402 of seeds 112 are laid out in the tumor. The radial angles may be spaced evenly by about the same angle or may be spaced unevenly. The pivot points are optionally all included on a straight line, at different depths of insertion of delivery tube 102 into the tumor.

In some embodiments, in all the layers 402, a same number of seeds 112 are ejected into the tumor, in a same radial layout. Alternatively, different layouts and/or different numbers of seeds 112 may be used in different depths, for example depending on the size and/or shape of the tumor. In some embodiments, the movement from the first depth to subsequent depths is in an insertion direction, such that the first depth is closest to a point of entrance of delivery tube 102 into the tumor. Alternatively, the movement from the first depth to subsequent depths is in a retraction direction, and the first depth is selected to be farthest from the point of entrance of delivery tube 102 into the tumor.

During the method of FIG. 7, when the seeds 112 in applicator 106 were all ejected, applicator 106 is optionally removed from delivery tube 102 and replaced by a different applicator 106 which is loaded with additional seeds 112. The replacement is optionally carried out, while delivery tube 102 is within the tumor. If the replacement applicator 106 is loaded with seeds 112 of a different length than those previously used with the removed applicator 106, handle 306 is optionally also replaced to one with slots 310 spaced in a manner matching the lengths of the seeds 112 in the replacement applicator 106.

In some embodiments, after ejecting the seeds 112, one or more seeds 112 are implanted along the axis of delivery tube 102. These embodiments are optionally used when the area of the tumor occupied by delivery tube 102 during the implantation of the seeds 112 remains distanced from the seeds 112 implanted radially. It is noted, however, that in some cases, after removing delivery tube 102 seeds 112 implanted in the tumor move back with tumor tissue to occupy the area in which delivery tube 102 was located. In such cases, seeds 112 on the axis may not be required.

In some embodiments, before implanting the seeds in the tumor, a layout plan is prepared, e.g., by a processor, with intended locations of the seeds in the tumor. Optionally, the dose reaching each point in the tumor is estimated to verify that a sufficient dose will reach every point in the tumor. In some embodiments, the area of the tumor is determined, for example from a medical image of the surroundings of the tumor and accordingly the area is determined. According to a type of the tumor, as discussed for example in PCT application PCT/IB2022/055322, titled: "Activity Levels for Diffusing Alpha-Emitter Radiation Therapy", which is incorporated herein by reference in its entirety, a size of a cylinder that can be covered by implanted layers of seeds is determined. Thereafter a minimum number of cylindrical regions, and corresponding insertion points of delivery tube 102 are determined. For each cylindrical region, the length of the region is determined and accordingly a number of layers to cover the region is selected. Accordingly, the processor presents to the user instructions on the seeds to be implanted.

Each seed 112 optionally has a length of at least 0.1 centimeters, 0.2 centimeters, 0.5 centimeters or even at least 0.8 centimeters. Optionally, seed 112 is shorter than 2.1 centimeters, or even shorter than 1.5 or 1.2 centimeters. In some embodiments, seed 112 has a length of about 1 centimeter. The seeds may all have the same length, or different seeds may have different lengths. In some embodiments, instead of using seeds of different lengths, a plurality of seeds are ejected in a single radial angle in directions where the tumor is large.

The seeds 112 optionally have an outer diameter of at least 0.3 millimeters, at least 0.5 millimeters, or even at least 0.6 millimeters. In some embodiments, seeds 112 have an outer diameter of about 0.7 millimeters, while in other embodiments seeds 112 have an outer diameter of 0.35 millimeters. The inner diameter of seeds 112 is optionally greater than 0.2 millimeters, greater than 0.4 millimeters or even greater than 0.5 millimeters. In some embodiments, the inner diameter of seeds 112 is smaller than 2 millimeters, smaller than 1 millimeter or even smaller than 0.5 millimeters. In some embodiments, the internal diameter is about 0.25 millimeters or 0.4 millimeters. Seeds 112 may all have the same diameter, or different seeds may have different diameters.

The Tubular seeds 112 optionally have a length of at least 2 times, at least 5 times or even at least ten times their outer diameter. Seeds 112 optionally comprise stainless steel, for example 316LVM stainless steel, Titanium, Nitinol, Zirconia, Alumina and/or any other suitable biocompatible material. In some embodiments, seeds 112 are formed of a conductive material to allow attachment of the radionuclides to the seeds using methods requiring a conductive seed. Alternatively, a non-conductive material is used for seeds 112 and other suitable methods are used to attach the radionuclides to the seed, such as a suitable thin coating.

Seeds 112 are loaded with particles of a radioactive substance. Optionally, the radioactive substance comprises alpha emitting atoms on an outer surface of seed 112. The particles are mounted on the seed using any method known in the art, including any of the methods described in U.S. Pat. No. 8,834,837 to Kelson et al., titled: "Method and Device for Radiotherapy", and US patent publication 2009/0136422 to Kelson et al., titled: "Radioactive Surface Source and a Method for Producing the Same", which are incorporated herein by reference in their entirety. In some embodiments, the seeds carry Radium-223 or Radium-224 particles. Alternatively, the seeds carry other suitable particles, such as Radon-219, Radon-220 or Thorium-228. In one specific embodiment, seeds 112 comprise up to 5 µCi and/or up to 185 kBq of Radium 224. In other embodiments, seed 112 carries higher levels of activity. It is noted, however, that in still other embodiments, seed 112 is loaded with other amounts of radioactive substances or with other radioactive substances which emit other particles, such as beta and/or gamma particles.

FIG. 8 is a schematic illustration of a preloaded applicator 106 during delivery, before use, in accordance with an embodiment of the present invention. At the time of delivery, applicator 106 is preloaded with radioactive seeds 112. In order to avoid leakage of radionuclides from applicator 106, applicator 106 is optionally sealed on both its proximal and distal ends, as discussed herein below.

On the proximal end of applicator 106, hub 124 includes silicone sheet 142 (FIG. 1) which seals the proximal end of applicator 106. On its distal end, applicator 106 connects to an extension tube 602 (FIG. 9) which extends beyond the area including seeds 112, and this extension tube 602 is configured to be filled with a liquid which traps radionuclides from the seeds and prevents them from leaving applicator 106. Extension tube 602 is covered by a distal hub 604 of applicator 106.

In some embodiments, preloaded applicator 106 is provided from the manufacture site with the liquid which traps radionuclides already in applicator 106. These embodiments, may be used, for example, when sterilization is performed using gamma rays, which do not require high temperatures which would boil the liquid. In other embodiments, in order to allow for sterilization at a temperature higher than the boiling point of the liquid, the liquid is introduced into applicator 106 before its sealing is removed, immediately before the method of implanting the seeds 112 begins.

FIG. 9 is a schematic illustration of distal hub 604, in accordance with an embodiment of the invention, in which the liquid is introduced immediately before the implanting procedure. Distal hub 604 comprises a tube connection hub 608, which connects applicator 106 to extension tube 602. Distal hub 604 further includes a seed stopper 610, which prevents seeds 112 from leaving applicator 106. Seed stopper 610 optionally comprises a suitable heat resistant material, such as polyetheretherketon (also known as PEEK). Distal hub 604 further includes a distal silicone sheet 612, held between two screws 614 and 616, sealing applicator 106 on its distal end. Finally, distal hub 604 comprises a syringe hub 618.

In preparation for use, a syringe (not shown) including a suitable liquid for trapping radionuclides is attached to syringe hub 618, and stylet 114 is retracted a suitable extent (e.g., 40 millimeters) from applicator 106 to reduce pressure in applicator 106. Then, the liquid from the syringe is filled into extension tube 602 and therefrom, due to the low pressure in applicator 106, into applicator 106 in a manner which surrounds seeds 112. Thereafter, extension tube 602 is detached from applicator 106, for example by cutting it in a cutting slot 620 of distal hub 604, and distal hub 604 is removed from applicator 106. The liquid surrounding seeds 112, within applicator 106, prevents radon from escaping from applicator 106 and also holds seeds 112 in place and prevents them from undesired movements.

In some embodiments, the liquid is a biocompatible viscous liquid such as glycerine. In other embodiments, for example when treating a tumor in the brain, the liquid comprises a brain tissue compatible material, such as saline. Optionally, extension tube 602 has a length of at least 5 millimeters, or at least 8 millimeters, for example 10 millimeters. The liquid in extension tube 602 oy has a volume of about 1 microliter.

FIG. 10 is a cross section of a delivery tube system 700, in accordance with anther embodiment of the invention. Unlike delivery tube 102 of FIG. 1, which has a side window 110 through which a distal end of applicator 106 exits, in delivery tube system 700 applicator 106 exits through the distal end. Delivery tube system 700 comprises a delivery tube 702 and a trocar 704 within an internal channel of delivery tube 702.

In use, delivery tube system 700 is first inserted to the patient, with trocar 704 within delivery tube 702. After reaching a desired pivot point for installing seeds 112, trocar 704 is removed from deliver tube 702 and applicator 106 is inserted into delivery tube 702 to implant the seeds at an angle to delivery tube 702 to form a cone-shaped layout of seeds. Before or after implanting seeds 112 at an angle, one or more seeds 112 may be implanted on axis, using applicator 106 are a different applicator which does not bend.

CONCLUSION

While the above description relates to use of biocompatible materials, the invention is not limited to such materials and in those cases in which it is medically permissible to use non-biocompatible materials, for example for elements that do not come in contact with sensitive patient tissue, such non-biocompatible materials may be used.

It will be appreciated that the above described methods and apparatus are to be interpreted as including apparatus for carrying out the methods and methods of using the apparatus. It should be understood that features and/or steps described with respect to one embodiment may sometimes be used with other embodiments and that not all embodiments of the invention have all of the features and/or steps shown in a particular figure or described with respect to one of the specific embodiments. Tasks are not necessarily performed in the exact order described.

The terminology used herein is for the purpose of describing particular embodiments only and is not intended to be limiting of the invention. As used herein, theterm "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

It is noted that some of the above described embodiments may include structure, acts or details of structures and acts that may not be essential to the invention and which are described as examples. Structure and acts described herein are replaceable by equivalents which perform the same function, even if the structure or acts are different, as known in the art. The embodiments described above are cited by way of example, and the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art. Therefore, the scope of the invention is limited only by the elements and limitations as used in the claims.

The invention claimed is:

1. A method of inserting radiotherapy seeds into a tumor, comprising:
   inserting a delivery tube to a first depth in the tumor;
   ejecting a plurality of radiotherapy seeds from the delivery tube into the tumor, while the delivery tube is at the first depth, wherein each of the plurality of radiotherapy seeds is ejected at an angle relative to an axis of the delivery tube, and wherein the plurality of radiotherapy seeds are ejected in at least two different radial angles; and
   moving the delivery tube to a second depth in the tumor and ejecting one or more radiotherapy seeds from the delivery tube into the tumor at the second depth.

2. The method as in claim 1, wherein ejecting the plurality of radiotherapy seeds comprises ejecting the plurality of radiotherapy seeds at an angle between 10° and 25° relative to the axis of the delivery tube.

3. The method as in claim 1, wherein ejecting the plurality of radiotherapy seeds comprises rotating the delivery tube while the delivery tube is at the first depth, in order to eject radiotherapy seeds to different radial angles.

4. The method as in claim 1, wherein the plurality of radiotherapy seeds ejected at the first depth have a length of at least 5 millimeters, and wherein ejecting one or more radiotherapy seeds from the delivery tube into the tumor at the second depth comprises ejecting in the second depth radiotherapy seeds that are shorter than the plurality of radiotherapy seeds ejected at the first depth.

5. The method as in claim 4, wherein ejecting in the second depth comprises ejecting in the second depth radiotherapy seeds that are shorter than 4 millimeters.

6. The method as in claim 1, wherein a same number of radiotherapy seeds are ejected from the first and second depths.

7. The method as in claim 6, wherein the radiotherapy seeds in the first depth are ejected at different radial angles than the radiotherapy seeds of the second depth.

8. The method as in claim 1, wherein ejecting the plurality of radiotherapy seeds comprises ejecting the plurality of radiotherapy seeds from an elongate applicator by pushing a stylet in the elongate applicator while holding the elongate applicator stationary.

9. The method as in claim 1, wherein ejecting the plurality of radiotherapy seeds comprises ejecting the plurality of radiotherapy seeds from an elongate applicator by holding a stylet stationary in the elongate applicator while retracting the elongate applicator.

10. The method as in claim 1, wherein ejecting the plurality of radiotherapy seeds comprises ejecting the plurality of radiotherapy seeds at an angle between 5° and 15° relative to the axis of the delivery tube.

11. The method as in claim 1, further comprising implanting one or more radiotherapy seeds along the axis of the delivery tube.

* * * * *